(12) United States Patent
Bhat et al.

(10) Patent No.: US 10,047,071 B1
(45) Date of Patent: Aug. 14, 2018

(54) DIHYDROPYRIMIDINONE DERIVATIVES

(71) Applicant: KING SAUD UNIVERSITY, Riyadh (SA)

(72) Inventors: Mashooq Ahmad Bhat, Riyadh (SA); Mohamed A. Al-Omar, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/871,927

(22) Filed: Jan. 15, 2018

(51) Int. Cl.
*C07D 403/10* (2006.01)

(52) U.S. Cl.
CPC .................. *C07D 403/10* (2013.01)

(58) Field of Classification Search
None
See application file for complete search history.

(56) References Cited

U.S. PATENT DOCUMENTS

| | | | |
|---|---|---|---|
| 4,218,452 A | 6/1980 | Lopez et al. | |
| 6,335,340 B1 | 1/2002 | Gallagher et al. | |
| 8,518,975 B2 * | 8/2013 | Aslanian ............. | C07D 237/14 514/341 |
| 8,546,393 B2 | 10/2013 | Albert et al. | |
| 9,115,093 B2 | 8/2015 | Gnamm et al. | |
| 9,119,856 B1 | 9/2015 | Al-Dhfyan et al. | |
| 9,440,930 B2 | 9/2016 | Oost et al. | |
| 9,856,232 B1 | 1/2018 | Bhat et al. | |
| 2005/0215790 A1 | 9/2005 | Srinivasan et al. | |
| 2008/0145453 A1 | 6/2008 | Lopez et al. | |

FOREIGN PATENT DOCUMENTS

| WO | WO 2006/038001 | 4/2006 |
|---|---|---|
| WO | WO 2010/046780 | 4/2010 |

OTHER PUBLICATIONS

Pathan et al., "Solid supported microwave induced synthesis of imidazole-pyrimidine hybrids: Antimicrobial evaluation and docking study as 14DM-CPY51 Inhibitors," Arabian Journal of Chemistry, 9, pp. S100-S108, available online Feb. 19, 2011.

Q.Zhang et al., "Design, synthesis, linear and nonlinear photophysical properties of novel pyrmidine-based imidazole derivatives," New Journal of Chemistry, 40(4), pp. 3456-3463, Feb. 10, 2016.

* cited by examiner

*Primary Examiner* — Po-Chih Chen
(74) *Attorney, Agent, or Firm* — Richard C. Litman

(57) ABSTRACT

A dihydropyrimidinone derivative includes a compound having a chemical structure according to Formula 1:

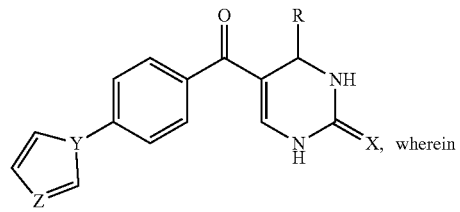

Formula 1 wherein

Z is selected from O, S and N;
Y is N
X is selected from O and S; and
R represents aryl, substituted aryl, heteroaryl, or substituted heteroaryl, wherein the substituted aryl or substituted heteroaryl have one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

11 Claims, 1 Drawing Sheet

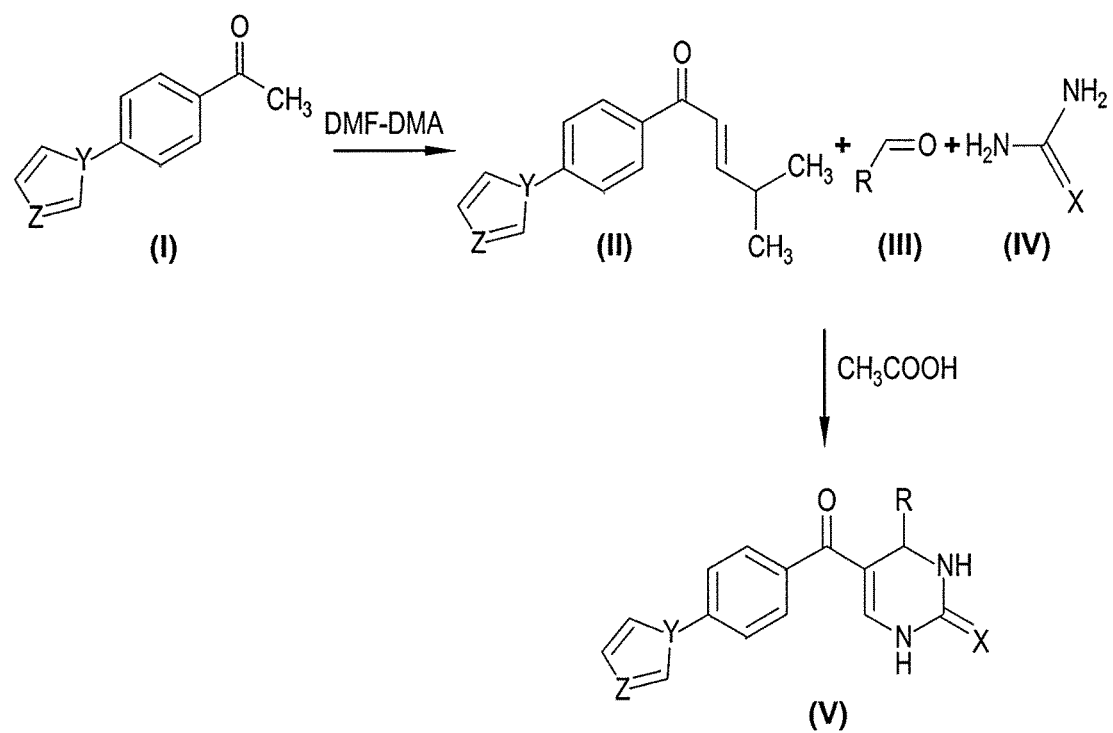

DIHYDROPYRIMIDINONE DERIVATIVES

BACKGROUND

1. Field

The disclosure of the present patent application relates to dihydropyrimidinone derivatives, and particularly to 5-[4-(1H-imidazol-1-yl) benzoyl]-4-substituted phenyl-3,4-dihydropyrimidin-2(1H)-one derivatives.

2. Description of the Related Art

Imidazole is an important five-membered aromatic pharmacophore widely present in natural products and synthetic molecules. The special structural feature of the imidazole ring with desirable electron-rich features is beneficial for imidazole derivatives to readily bind with a variety of enzymes and receptors.

Numerous imidazole-based compounds have been extensively used to treat various types of diseases. Imidazole-based compounds can provide various biological activities, e.g., anticancer, antifungal, antibacterial, anti-tubercular, anti-inflammatory, anti-neuropathic, antihypertensive, antihistaminic, anti-parasitic, anti-obesity, and antiviral activities. A series of substituted aryloxy alkyl and aryloxy aryl alkyl imidazoles were synthesized and evaluated in vitro as anti-leishmanial against *Leshmania donovani*. A series of novel 5-(nitro/bromo)-styryl-2-benzimidazoles derivatives and screened for in vitro anti-tubercular activity against *Mycobacterium tuberculosis*. 2-substituted-4, 5-diphenyl-1H-imidazoles exhibited anti-inflammatory activity based on Carrageenan-induced paw edema method. 2-(substituted phenyl)-1H-imidazole and (substituted phenyl)-[2-(substituted phenyl)-imidazol-1-yl]-menthanone analogues exhibited antimicrobial activity against Gram positive, Gram negative and fungal species.

Pyrimidines have played an important role in medicinal chemistry [Folkers K, et al., *J. Am. Chem. Soc.*, 1.932; 54: 3751-3758]. Pyrimidines are an important scaffold in the field of medicinal chemistry because of their potential biological activities such as anti-tumor, anti-virus and anti-bacterial agents [Singh K, et al., *J. Med. Chem.* 1992, 35, 4751-4763; Singh K, et al., *J. Med. Chem.* 1991, 34, 806-811; Rovnyak G, et al., *J. Med. Chem.* 1995, 38, 119-129]. Some pyrimidines have been used as anti-hypertensive agents. 4-Aryl-1,4-dihydropyridines, like Nifedipine, was first introduced as antihypertensive into clinical medicine in 1975. Dihydropyridines are the most potent calcium channel modulators available for the treatment of various cardiovascular diseases [Rana K, et al., *Ind. J. Chem.* 2004, 43 B, 1553-1557].

Substituted dihydropyrimidinine compounds show interesting biological properties. Some of the analogs of dihydropyrimidine compounds are antitumor agents. Dihydropyrimidinones have emerged as the integral back bone of calcium channel blockers (Rovnyak, G. C. et al., *J. Med. Chem.* 1995, 38, 119-129) and antihypertensive agents (Atwal, K. S. et al., *J. Med. Chem.* 1991, 34, 806-811). These compounds exhibit a broad range of biological activities such as antiviral, antitumor, antibacterial and anti-inflammatory (Kappe, C. O. Tetrahedron, 1993, 49, 6937-6963).

Dihydropyrimidinone compounds were first synthesized by Pietro Biginelli. The type of compounds were known as Biginelli compounds. The process comprised reacting numerous aldehydes with urea and a beta-keto ester to give a tetrahydropyrimidinone. Dihydropyrimidines or Biginelli's compounds have been associated with a broad spectrum of biological activities, including therapeutic agents against ulcerative colitis, inhibitors of neutrophil elastase activity, agents for treatment of cardiovascular diseases, agents for treating chronic wounds, inhibitors of neutrophil elastase activity, agents for treatment of Hunner's ulcer, and agents for treating cancer.

Thus, a process for preparing imidazole linked dihydropyrimidinone derivatives solving the aforementioned problems is desired.

SUMMARY

Dihydropyrimidinone derivatives include 5-[4-(1H-imidazol-1-yl) benzoyl]-4-substituted phenyl-3,4-dihydropyrimidin-2(1H)-one derivatives having a chemical structure according to Formula 1:

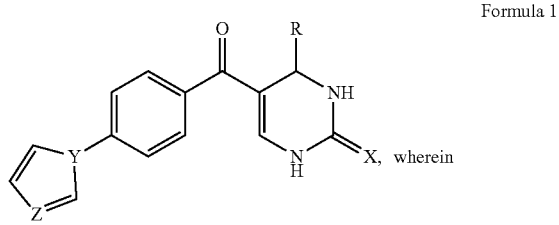

Formula 1

Z is selected from O, S and N;
Y is N
X is selected from O and S; and
R represents aryl, substituted aryl, heteroaryl, or substituted heteroaryl, wherein the substituted aryl or substituted heteroaryl have one or more substituents selected from halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

An embodiment of the present subject matter is directed to a method of making a dihydropyrimidinone derivative, including refluxing 1-[4-(1H-imidazol-1-yl) phenyl]-ethan-1-one (0.01 mol) with dimethylforamide dimethylacetal (DMF-DMA) (0.013 mol) to obtain enaminone; and refluxing a solution of enaminone (0.01 mol), substituted benzaldehyde (0.01 mol), and urea (0.01 mol) to yield dihydropyrimidinone derivatives having a structure of:

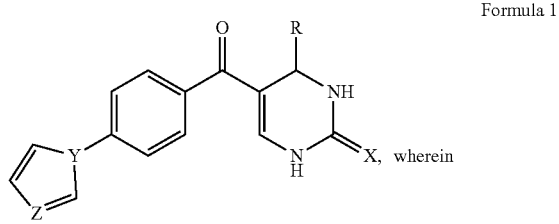

Formula 1

Z is selected from O, S and N;
Y is N
X is selected from O and S; and
R represents an aryl, substituted aryl, heteroaryl, or substituted heteroaryl, wherein the substituted aryl or substituted heteroaryl have one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

These and other features of the present disclosure will become readily apparent upon further review of the following specification and drawings.

BRIEF DESCRIPTION OF THE DRAWINGS

The sole drawing FIGURE illustrates the reaction scheme by which the dihydropyrimidinone derivatives can be prepared.

DETAILED DESCRIPTION OF THE PREFERRED EMBODIMENTS

A dihydropyrimidinone derivative includes a compound having a chemical structure according to Formula 1, shown below.

Formula 1 wherein

Z is selected from O, S and N;
Y is N;
X is selected from O and S; and
R represents an aryl, substituted aryl, heteroaryl, or substituted heteroaryl, wherein the substituted aryl or substituted heteroaryl have one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

In an embodiment, R represents mono- or di-substituted phenyl compounds. In an embodiment, R is selected from phenyl, 2-nitrophenyl, 3-nitrophenyl, 4-nitrophenyl, 4-chlorophenyl, 2,4-dichlorophenyl, 2-methoxyphenyl, 4-hydroxyphenyl, 3-methoxyphenyl, 2,4,5-trimethoxy phenyl, 2,3,4-trimethoxy phenyl, 3,4,5-trimethoxy phenyl, 2,4,6-trimethoxy phenyl, and 2,4-dimethoxy phenyl.

The dihydropyrimidinone derivatives can include 5-[4-(1H-imidazol-1-yl) benzoyl]-4-substituted phenyl-3,4-dihydropyrimidin-2(1H)-one. In an embodiment of the present subject matter, the dihydropyrimidinone derivatives include compounds (1-15) provided below:

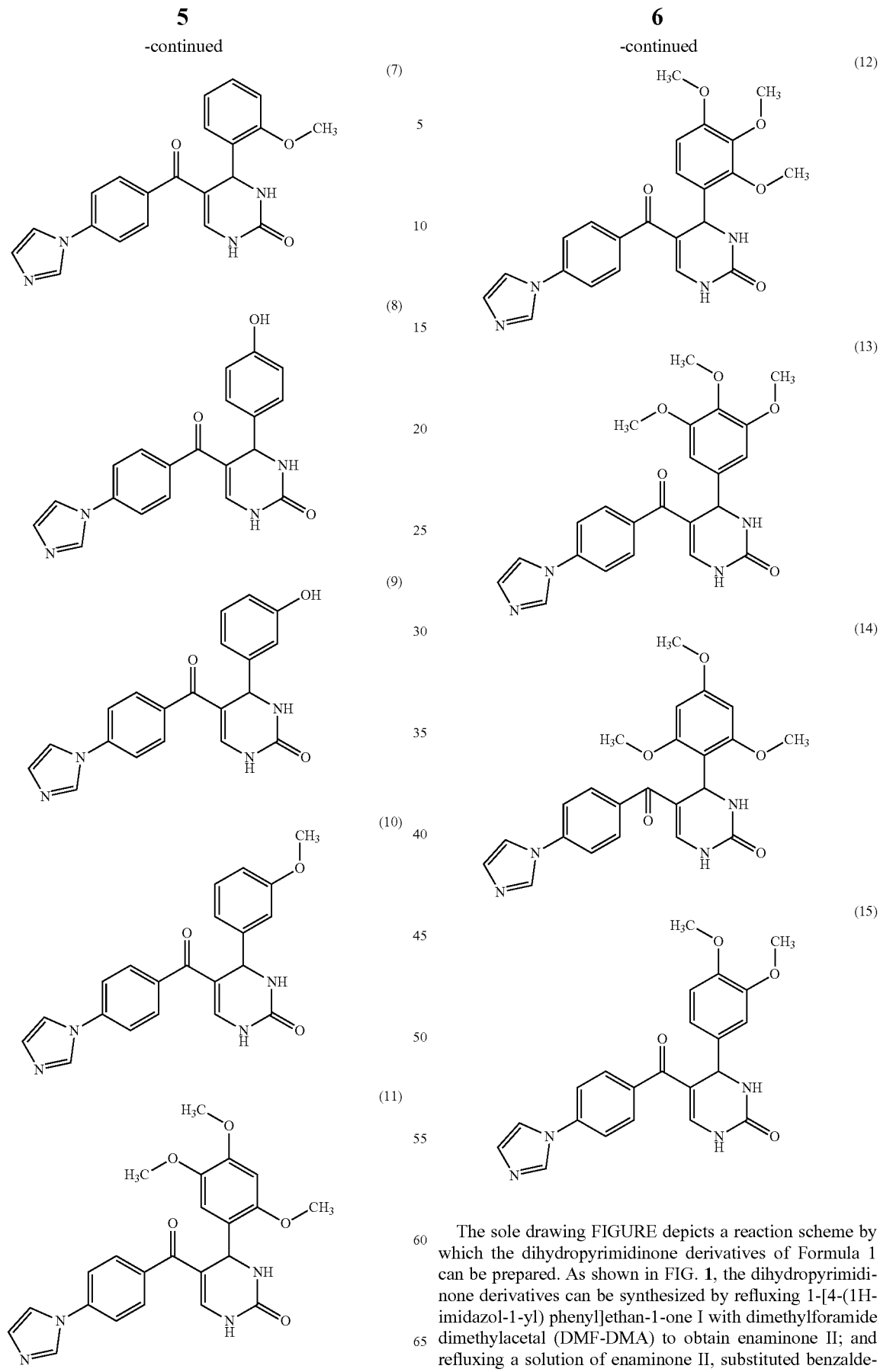

The sole drawing FIGURE depicts a reaction scheme by which the dihydropyrimidinone derivatives of Formula 1 can be prepared. As shown in FIG. 1, the dihydropyrimidinone derivatives can be synthesized by refluxing 1-[4-(1H-imidazol-1-yl) phenyl]ethan-1-one I with dimethylforamide dimethylacetal (DMF-DMA) to obtain enaminone II; and refluxing a solution of enaminone II, substituted benzaldehydes III, urea IV, and Glacial acetic acid to yield the dihydropyrimidinone derivatives V of Formula 1, where X, Y, Z and R represent the molecules disclosed above.

In an embodiment, the 1-[4-(1H-imidazol-1-yl) phenyl] ethan-1-one is refluxed with the dimethylforamide dimethylacetal (DMF-DMA) under a solvent free condition for about 10 hours to obtain enaminone II.

In an embodiment, the solution of enaminone, substituted benzaldehyde, urea, and Glacial acetic acid is refluxed for about 3 hours.

In an embodiment, the method of preparing the dihydropyrimidinone derivatives further includes recrystallizing the 5-[4-(1H-imidazol-1-yl)benzoyl]-4-substituted phenyl-3,4-dihydropyrimidin-2(1H)-one derivatives from the ethanol and Glacial acetic acid mixture to yield the dihydropyrimidinone derivatives V of Formula 1.

The dihydropyrimidinone derivatives can provide one or more therapeutic benefits. For example, the dihydropyrimidinone derivatives can be used as an active ingredient in a pharmaceutical composition for treatment of one or more ailments, including hypertension. It is anticipated that the dihydropyrimidinone derivatives can be effective anti-hypertensive agents, as the combined presence of the dihydropyrimidine and imidazole moieties can provide synergistic anti-hypertensive effects. A pharmaceutical composition can include one or more of the dihydropyrimidinone derivatives, or salt thereof, and a pharmaceutical carrier. The pharmaceutical composition including the one or more dihydropyrimidinone derivatives can be prepared and administered in any suitable manner, such as that described in U.S. Pat. No. 9,856,232, issued Jan. 2, 2018 to Bhat et al., which is hereby incorporated by reference in its entirety.

The following examples are provided by way of illustration.

Example 1

Synthesis of the Dihydropyrimidinone Derivatives

As shown in the sole drawing FIGURE, enaminone (II), (2E)-1-[4-(1H-imidazol-1-yl)phenyl]-4-methylpent-2-en-1-one was synthesized by refluxing 1-[4-(1H-imidazol-1-yl) phenyl]ethan-1-one (I) with dimethylforamide dimethylacetal (DMF-DMA) under solvent free conditions for 10 hours.

To prepare the final dihydropyrimidinone derivatives, a solution of enaminone (II) (0.01 mol), substituted benzaldehyde (0.01 mol) III, urea (0.01 mol) IV, and Glacial acetic acid (10 mL) was heated under reflux for 3 hours to form precipitates. The precipitates (Compounds 1 to 15) thus formed were collected by filtration, washed with water, and recrystallized from a Glacial acetic acid and ethanol mixture. In the $^1$H-NMR spectra, the signals of the individual protons of the compounds were verified on the basis of multiplicity, chemical shifts and the coupling constant. Analytical and spectral data for the compounds were in good agreement with the expected structures of the compounds.

The spectral data for compounds 1 to 15 are provided below:

5-[4-(1H-imidazol-1-yl)benzoyl]-4-phenyl-3,4-dihydropyrimidin-2(1H)-one (1)

Yield: 75%; m.p.: 130-132° C.; IR (KBr) cm$^{-1}$: 3110 (NH str.), 1700 (C=O), 1601 (C=O), 1476 (C=C), 1214 (C—O); $^1$H NMR (500 MHz, DMSO-d$_6$): δ=6.12 (1H, d, J=2.5 Hz, C-4), 7.14 (1H, s, imidazole H), 7.53 (1H, s, imidazole H), 7.54-7.94 (9H, m, Ar—H), 7.95 (1H, s, imidazole H), 8.30 (1H, s, NH, D$_2$O exchg.) 8.49 (1H, s, =CH), 9.66 (1H, s, NH, D$_2$O exchg.); $^{13}$C NMR (125.76 MHz, DMSO-d$_6$): δ=56.4, 60.7, 116.6, 118.2, 120.1, 124.5, 130.0, 130.4, 130.6, 132.4, 134.4, 136.1, 136.6, 138.6, 143.0, 148.3, 150.8, 153.2, 190.6; MS: m/z=345.03 [M+1]$^+$; Analysis: for C$_{20}$H$_{16}$N$_4$O$_2$, calcd. C, 69.76, H, 4.68, N, 16.27%; found C, 69.96, H, 4.69, N, 16.31%.

5-[4-(1H-imidazol-1-yl)benzoyl]-4-(2-nitrophenyl)-3,4-dihydropyrimidin-2(1H)-one (2)

Yield: 80%; m.p.: 155-157° C.; IR (KBr) cm$^{-1}$: 3109 (NH str.), 1700 (C=O), 1599 (C=O), 1516 (C=C), 1245 (C—O); $^1$H NMR (500 MHz, DMSO-d$_6$): δ=5.61 (1H, s, C-4), 7.14 (1H, s, imidazole H), 7.20 (1H, s, imidazole 7.66-7.84 (8H, m, Ar—H), 7.93 (1H, s, imidazole H), 8.23 (1H, s, NH, D$_2$O exchg.) 8.37 (1H, s, =CH), 9.67 (1H, s, NH, D$_2$O exchg.); $^{13}$C NMR (125.76 MHz, DMSO-d$_6$): δ=53.0, 56.2, 111.3, 118.0, 120.1, 123.5, 124.0, 128.2, 129.5, 130.1, 130.5, 130.4, 136.0, 136.5, 139.0, 143.0, 147.1, 151.2, 151.2, 190.6; MS: m/z=389.58 [M]$^+$; Analysis: for C$_{20}$H$_{15}$N$_5$O$_4$, calcd. C, 61.69, H, 3.88, N, 17.99%; found C, 61.87, H, 3.89, N, 17.95%.

5-[4-(1H-imidazol-1-yl)benzoyl]-4-(4-nitrophenyl)-3,4-dihydropyrimidin-2(1H)-one (3)

Yield: 80%; m.p.: 158-160° C.; IR (KBr) cm$^{-1}$: 3107 (NH str.), 1700 (C=O), 1599 (C=O), 1512 (C=C), 1181 (C—O); $^1$H NMR (500 MHz, DMSO-d$_6$): δ=5.61 (1H, s, C-4), 7.14 (1H, s, imidazole H), 7.20 (1H, s, imidazole H), 7.66-7.84 (8H, m, Ar—H), 7.93 (1H, s, imidazole H), 8.23 (1H, s, NH, D$_2$O exchg.) 8.37 (1H, s, =CH), 9.67 (1H, s, NH, D$_2$O exchg.); $^{13}$C NMR (125.76 MHz, DMSO-d$_6$): δ=53.7, 56.5, 111.7, 118.3, 120.2, 123.9, 124.3, 128.4, 129.6, 130.4, 130.7, 130.9, 136.1, 136.8, 139.2, 143.0, 147.2, 151.3, 151.5, 190.7; MS: m/z=390.17 [M+1]$^+$; Analysis: for C$_{20}$H$_{15}$N$_5$O$_4$, calcd. C, 61.69, H, 3.88, N, 17.99%; found C, 61.51, H, 3.87, N, 17.96%.

5-[4-(1H-imidazol-1-yl)benzoyl]-4-(3-nitrophenyl)-3,4-dihydropyrimidin-2(1H)-one (4)

Yield: 82%; m.p.: 160-162° C.; IR (KBr) cm$^{-1}$: 3447 (NH str.), 1700 (C=O), 1654 (C=O), 1609 (C=C), 1057 (C—O); $^1$H NMR (500 MHz, DMSO-d$_6$): δ=5.64 (1H, s, C-4), 7.14 (1H, s, imidazole H), 7.25 (1H, s, imidazole H), 7.62-7.87 (8H, m, Ar—H), 7.87 (1H, s, imidazole H), 8.22 (1H, s, NH, D$_2$O exchg.) 8.37 (1H, s, =CH), 9.71 (1H, s, NH, D$_2$O exchg.); $^{13}$C NMR (125.76 MHz, DMSO-d$_6$): δ=53.6, 56.5, 111.7, 115.8, 118.3, 120.2, 121.8, 122.7, 122.9, 130.1, 130.4, 130.6, 130.7, 133.8, 136.1, 136.8, 137.5, 139.1, 139.2, 140.7, 143.2, 146.5, 148.2, 151.4, 190.8; MS: m/z=390.11 [M+1]$^+$; Analysis: for C$_{20}$H$_{15}$N$_5$O$_4$, calcd. C, 61.69, H, 3.88, N, 17.99%; found C, 61.58, H, 3.86, N, 17.97%.

4-(4-chlorophenyl)-5-[4-(1H-imidazol-1-yl)benzoyl]-3,4-dihydropyrimidin-2(1H)-one (5)

Yield: 90%; m.p.: 180-182° C.; IR (KBr) cm$^{-1}$: 3410 (NH str.), 1700 (C=O), 1654 (C=O), 1604 (C=C), 1055 (C—O); $^1$H NMR (500 MHz, DMSO-d$_6$): δ=5.46 (1H, s, C-4), 7.13 (1H, s, imidazole H), 7.15 (1H, s, imidazole II), 7.39-7.76 (8H, m, Ar—H), 7.84 (1H, s, imidazole H), 7.96 (1H, s, NH, D$_2$O exchg.) 8.37 (1H, s, =CH), 9.53 (1H, s, NH, D$_2$O exchg.); $^{13}$C NMR (125.76 MHz, DMSO-d$_6$):

δ=53.4, 56.5, 112.3, 116.3, 118.3, 120.2, 128.5, 130.1, 130.3, 130.7, 131.1, 132.4, 136.0, 136.1, 137.0, 137.7, 139.0, 139.1, 140.0, 142.6, 143.4, 151.5, 190.8; MS: m/z=378.77 [M]$^+$; Analysis: for $C_{20}H_{15}ClN_4O_2$, calcd. C, 63.41, H, 3.99, N, 14.79%; found C, 63.60, H, 4.00, N, 14.83%.

4-(2,4-dichlorophenyl)-5-[4-(1H-imidazol-1-yl)benzoyl]-3,4-dihydropyrimidin-2(1H)-one (6)

Yield: 87%; m.p.: 138-140° C.; IR (KBr) cm$^{-1}$: 3111 (NH str.), 1700 (C=O), 1604 (C=O), 1618 (C=C), 1216 (C—O); $^1$H NMR (500 MHz, DMSO-d$_6$): δ=5.86 (1H, s, C-4), 7.16 (1H, s, imidazole H), 7.19 (1H, s, imidazole H), 7.53-7.77 (7H, m, Ar—H), 7.84 (1H, s, imidazole H), 7.93 (1H, s, NH, D$_2$O exchg.) 8.39 (1H, s, =CH), 9.63 (1H, s, NH, D$_2$O exchg.); $^{13}$C NMR (125.76 MHz, DMSO-d$_6$): δ=56.5, 110.9, 118.3, 120.2, 120.4, 128.2, 129.4, 130.4, 130.6, 131.5, 133.2, 133.6, 136.1, 136.8, 139.2, 140.1, 143.1, 150.9, 170.0, 172.1, 190.5; MS: m/z=414.30 [M+1]$^+$; Analysis: for $C_{20}H_{14}Cl_2N_4O_2$, calcd. C, 58.13, H, 3.41, N, 13.56%; found C, 58.30, H, 3.40, N, 13.52%.

5-[4-(1H-imidazol-1-yl)benzoyl]-4-(2-methoxyphenyl)-3,4-dihydropyrimidin-2(1H)-one (7)

Yield: 77%; m.p.: 140-142° C.; IR (KBr) cm$^{-1}$: 3136 (NH str.), 1700 (C=O), 1690 (C=O), 1618 (C=C), 1111 (C—O); $^1$H NMR (500 MHz, DMSO-d$_6$): δ=3.78 (3H, s, OCH$_3$), 5.75 (1H, s, C-4), 6.92 (1H, s, imidazole H), 7.10 (1H, s, imidazole H), 7.25-7.77 (8H, m, Ar—H), 7.84 (1H, s, imidazole H), 7.87 (1H, s, NH, D$_2$O exchg.) 8.40 (1H, s, =CH), 9.44 (1H, s, NH, D$_2$O exchg.); $^{13}$C NMR (125.76 MHz, DMSO-d$_6$): δ=49.6, 55.7, 111.3, 111.8, 112.0, 112.7, 118.3, 120.2, 120.3, 120.5, 120.7, 130.3, 130.7, 136.1, 137.2, 139.0, 142.83, 151.9, 157.3, 190.7, 193.1; MS: m/z=375.08 [M+1]$^+$; Analysis: for $C_{21}H_{18}N_4O_3$, calcd. C, 67.37, H, 4.85, N, 14.96%; found C, 67.57, H, 4.86, N, 14.92%.

4-(4-hydroxyphenyl)-5-[4-(1H-imidazol-1-yl)benzoyl]-3,4-dihydropyrimidin-2(1H)-one (8)

Yield: 65%; m.p.: 2102-12° C.; IR (KBr) cm$^{-1}$: 3411 (NH str.), 1700 (C=O), 1654 (C=O), 1619 (C=C), 1056 (C—O); $^1$H NMR (500 MHz, DMSO-d$_6$): δ=6.10 (1H, d, J=2.5 Hz, C-4), 7.14 (1H, s, imidazole H), 7.53 (1H, s, imidazole H), 7.54-7.94 (8H, m, Ar—H), 7.95 (1H, s, imidazole H), 8.30 (1H, s, NH, D$_2$O exchg.) 8.49 (1H, s, =CH), 9.66 (1H, s, NH, D$_2$O exchg.) 10.2 (1H, s, NH, D$_2$O exchg.); MS: m/z=361.44 [M+1]$^+$; Analysis: for $C_{20}H_{16}N_4O_3$, calcd. C, 66.66, H, 4.48, N, 15.55%; found C, 66.46, H, 4.47, N, 15.51%.

4-(3-hydroxyphenyl)-5-[4-(1H-imidazol-1-yl)benzoyl]-3,4-dihydropyrimidin-2(1H)-one (9)

Yield: 66%; m.p.: 190-192° C.; IR (KBr) cm$^{-1}$: 3421 (NH str.), 1717 (C=O), 1684 (C=O), 1600 (C=C), 1055 (C—O); $^1$H NMR (500 MHz, DMSO-d$_6$): δ=5.46 (1H, d, J=2.5 Hz, C-4), 7.13 (1H, s, imidazole H), 7.50 (1H, s, imidazole H), 7.52-7.90 (8H, m, Ar—H), 7.95 (1H, s, imidazole H), 8.30 (1H, s, NH, D$_2$O exchg.) 8.49 (1H, s, =CH), 9.66 (1H, s, NH, D$_2$O exchg.) 10.2 (1H, s, NH, D$_2$O exchg.); MS: m/z=360.98 [M]$^+$; Analysis: for $C_{20}H_{16}N_4O_3$, calcd. C, 66.66, H, 4.48, N, 15.55%; found C, 66.48, H, 4.46, N, 15.52%.

5-[4-(1H-imidazol-1-yl)benzoyl]-4-(3-methoxyphenyl)-3,4-dihydropyrimidin-2(1H)-one (10)

Yield: 68%; m.p.: 125-127° C.; IR (KBr) cm$^{-1}$: 3125 (NH str.), 1700 (C=O), 1602 (C=O), 1418 (C=C), 1248 (C—O); $^1$H NMR (500 MHz, DMSO-d$_6$): δ=3.75 (314, s, OCH$_3$), 5.46 (1H, s, C-4), 6.92 (1H, s, imidazole H), 6.97 (1H, s, imidazole H), 7.16-7.66 (8H, m, Ar—H), 7.76 (1H, s, imidazole H), 7.83 (1H, s, NH, D$_2$O exchg.) 8.41 (1H, s, =CH), 9.51 (1H, s, NH, D$_2$O exchg.); $^{13}$C NMR (125.76 MHz, DMSO-d$_6$): δ=53.7, 55.3, 112.6, 112.9, 113.0, 116.6, 118.3, 118.9, 120.2, 120.3, 120.4, 120.5, 130.2, 130.3, 130.9, 136.1, 137.1, 137.8, 139.0, 139.1, 141.3, 142.4, 145.9, 151.8, 159.7, 190.8, 193.1; MS: m/z=374.55 [M]$^+$; Analysis: for $C_{21}H_{18}N_4O_3$, calcd. C, 67.37, H, 4.85, N, 14.96%; found C, 67.58, H, 4.87, N, 14.93%.

5-[4-(1H-imidazol-1-yl)benzoyl]-4-(2,4,5-trimethoxyphenyl)-3,4-dihydropyrimidin-2(1H)-one (11)

Yield: 70%; m.p.: 135-137° C.; IR (KBr) cm$^{-1}$: 3421 (NH str.), 1700 (C=O), 1654 (C=O), 1604 (C=C), 1206 (C—O); $^1$H NMR (500 MHz, DMSO-d$_6$): δ=3.75 (9H, s, 3×OCH$_3$), 5.60 (1H, s, C-4), 6.75 (1H, s, imidazole H), 6.90 (1H, s, imidazole H), 7.15-7.60 (611, m, Ar—H), 7.75 (1H, s, imidazole 7.83 (1H, s, NH, D$_2$O exchg.) 8.38 (1H, s, =CH), 9.39 (1H, s, NH, D$_2$O exchg.); MS: m/z=434.80 [M]$^+$; Analysis: for $C_{23}H_{22}N_4O_5$, calcd. C, 63.59, H, 5.10, N, 12.90%; found C, 63.40, H, 5.11, N, 12.86%.

5-[4-(1H-imidazol-1-yl)benzoyl]-4-(2,3,4-trimethoxyphenyl)-3,4-dihydropyrimidin-2(1H)-one (12)

Yield: 72%; m.p.: 138-140° C.; IR (KBr) cm$^{-1}$: 3412 (NH str.), 1718 (C=O), 1654 (C=O), 1618 (C=C), 1248 (C—O); $^1$H NMR (500 MHz, DMSO-d$_6$): =3.78 (9H, s, 3×OCH$_3$), 5.45 (1H, s, C-4), 6.67 (1H, s, imidazole H), 6.70 (1H, s, imidazole H), 7.70-7.78 (6H, m, Ar—H), 7.85 (1H, s, imidazole H), 7.91 (1H, s, NH, D$_2$O exchg.) 8.39 (1H, s, =CH), 9.49 (1H, s, NH, D$_2$O exchg.); $^{13}$C NMR (125.76 MHz, DMSO-d$_6$): b=53.8, 56.3, 60.4, 60.6, 104.1, 105.2, 105.4, 106.1, 118.3, 120.3, 130.7, 131.0, 136.1, 137.1, 137.2, 138.0, 139.2, 139.8, 140.3, 142.7, 151.6, 153.3, 153.5, 191.0; MS: m/z=435.00 [M+1]$^+$; Analysis: for $C_{23}H_{22}N_4O_5$, calcd. C, 63.59, H, 5.10, N, 12.90%; found C, 63.48, H, 5.12, N, 12.85%.

5-[4-(1H-imidazol-1-yl)benzoyl]-4-(3,4,5-trimethoxyphenyl)-3,4-dihydropyrimidin-2(1H)-one (13)

Yield: 75%; m.p.: 128-130° C.; IR (KBr) cm$^{-1}$: 3117 (NH str.), 1700 (C=O), 1654 (C=O), 1604 (C=C), 1245 (C—O); $^1$H NMR (500 MHz, DMSO-d$_6$): δ=3.75 (9H, s, 3×OCH$_3$), 5.62 (1H, s, C-4), 6.76 (1H, s, imidazole H), 7.00 (1H, s, imidazole H), 7.16-7.61 (6H, m, Ar—H), 7.75 (1H, s, imidazole H), 7.83 (1H, s, NH, D$_2$O exchg.) 8.38 (1H, s, =CH), 9.39 (1H, s, NH, D$_2$O exchg.); $^{13}$C NMR (125.76 MHz, DMSO-d$_6$): δ=49.8, 56.2, 56.5, 60.6, 61.1, 61.3, 80.0, 112.3, 118.3, 120.3, 123.1, 129.7, 130.3, 130.7, 136.2, 137.2, 138.0, 139.0, 139.5, 142.0, 142.3, 151.6, 152.2, 153.4, 190.7; MS: in/z=434.00 [M]$^+$; Analysis: for $C_{23}H_{22}N_4O_5$, calcd. C, 63.59, H, 5.10, N, 12.90%; found C, 63.50, H, 5.09, N, 12.89%.

5-[4-(1H-imidazol-1-yl)benzoyl]-4-(2,4,6-trimethoxyphenyl)-3,4-dihydropyrimidin-2(1H)-one (14)

Yield: 74%; m.p.: 130-132° C.; IR (KBr) cm$^{-1}$: 3421 (NH str.), 1718 (C=O), 1654 (C=O), 1618 (C=C), 1149 (C—O); $^1$H NMR (500 MHz, DMSO-d$_6$): δ=3.75 (9H, s, 3×OCH$_3$), 5.61 (1H, s, C-4), 6.75 (1H, s, imidazole H), 7.10 (1H, s, imidazole H), 7.18-7.62 (6H, m, Ar—H), 7.72 (1H, s, imidazole H), 7.83 (1H, s, NH, D$_2$O exchg.) 8.38 (1H, s, =CH), 9.40 (1H, s, NH, D$_2$O exchg.); MS: m/z=434.60 [M]$^+$; Analysis: for C$_{23}$H$_{22}$N$_4$O$_5$, calcd. C, 63.59, H, 5.10, N, 12.90%; found C, 63.55, H, 5.08, N, 12.84%.

5-[4-(1H-imidazol-1-yl)benzoyl]-4-(3,4-dimethoxyphenyl)-3,4-dihydropyrimidin-2(1H)-one (15)

Yield: 75%; m.p.: 136-138° C.; IR (KBr) cm$^{-1}$: 3117 (NH str.), 1700 (C=O), 1654 (C=O), 1618 (C=C), 1138 (C—O); $^1$H NMR (500 MHz, DMSO-d$_6$): δ=3.76 (6H, s, 3×OCH$_3$), 5.45 (1H, s, C-4), 6.90 (1H, s, imidazole H), 7.18 (1H, s, imidazole H), 7.63-7.80 (7H, m, Ar—H), 7.84 (1H, s, imidazole H), 7.90 (1H, s, NH, D$_2$O exchg.) 8.38 (1H, s, =CH), 9.48 (1H, s, NH, D$_2$O exchg.); $^{13}$C NMR (125.76 MHz, DMSO-d$_6$): δ=53.4, 55.8, 55.9, 56.5, 110.9, 112.1, 112.7, 118.3, 118.7, 120.2, 120.3, 130.3, 136.1, 136.8, 137.2, 139.0, 139.1, 139.4, 142.2, 148.6, 149.0, 151.7, 190.9, 193.3; MS: m/z=404.21 [M]$^+$; Analysis: for C$_{22}$H$_{20}$N$_4$O$_4$, calcd. C, 65.34, H, 4.98, N, 13.85%; found C, 63.14, H, 4.99, N, 13.81%.

It is to be understood that the process for preparing imidazole linked dihydropyrimidinone derivatives is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A dihydropyrimidinone derivative is a compound of Formula 1:

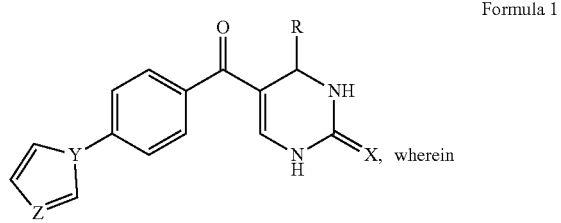

Formula 1

Z is N;
Y is N;
X is selected from O and S; and
R represents aryl, substituted aryl, heteroaryl, or substituted heteroaryl, wherein the substituted aryl or substituted heteroaryl have one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, arylamino, and or pharmaceutically acceptable salt thereof.

2. The dihydropyrimidinone derivative of claim 1, wherein R is mono-substituted phenyl or di-substituted phenyl.

3. The dihydropyrimidinone derivative of claim 1, wherein R is selected from phenyl, 2-nitrophenyl, 3-nitrophenyl, 4-nitrophenyl, 4-chlorophenyl, 2,4-dichlorophenyl, 2-methoxy phenyl, 4-hydroxyphenyl, 3-methoxyphenyl, 2,4,5-trimethoxyphenyl, 2,3,4-trimethoxy phenyl, 3,4,5-trimethoxyphenyl, 2,4,6-trimethoxyphenyl, and 2,4-dimethoxyphenyl.

4. The dihydropyrimidinone derivative of claim 1, wherein the dihydropyrimidinone derivative is a compound selected from the group consisting of:

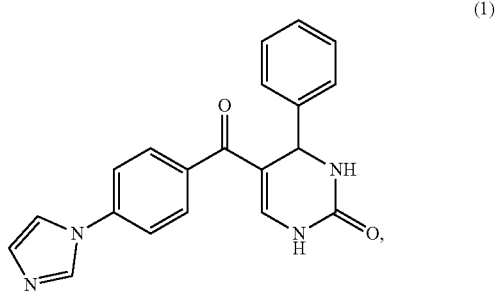

(1)

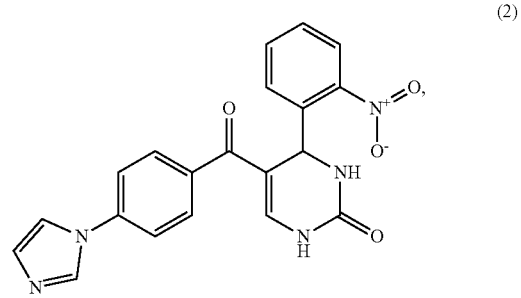

(2)

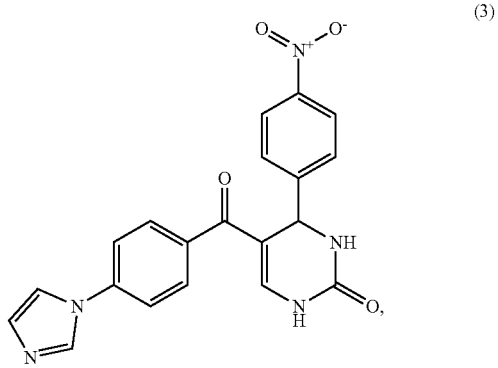

(3)

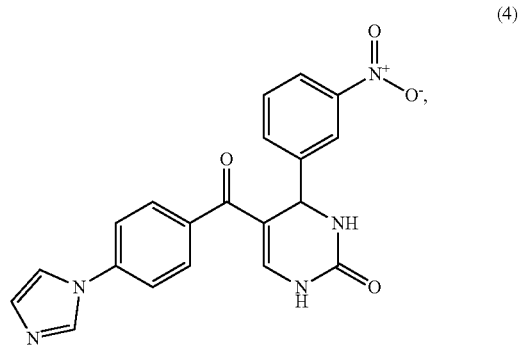

(4)

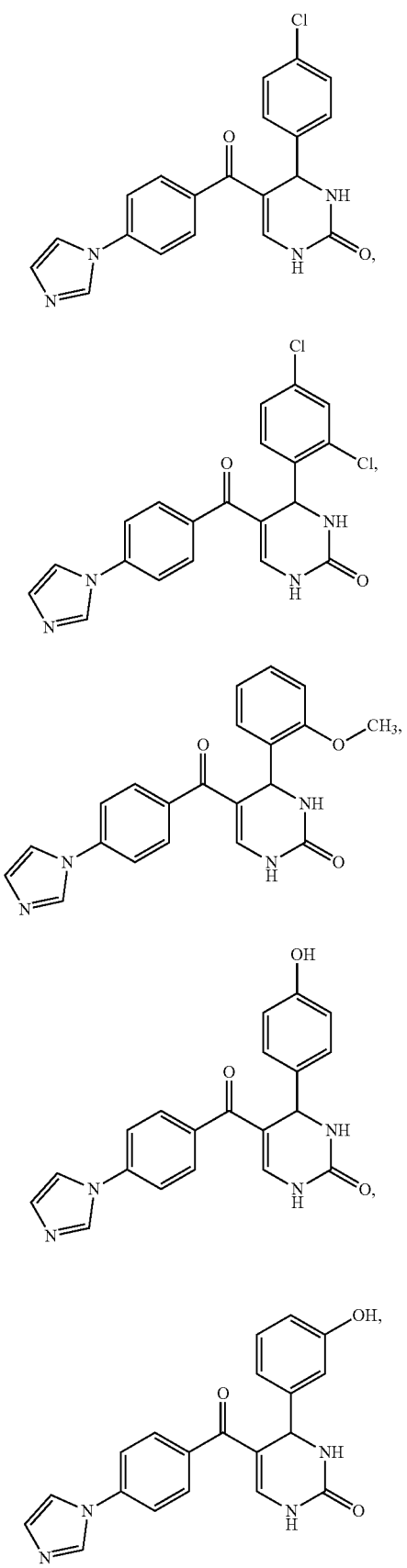
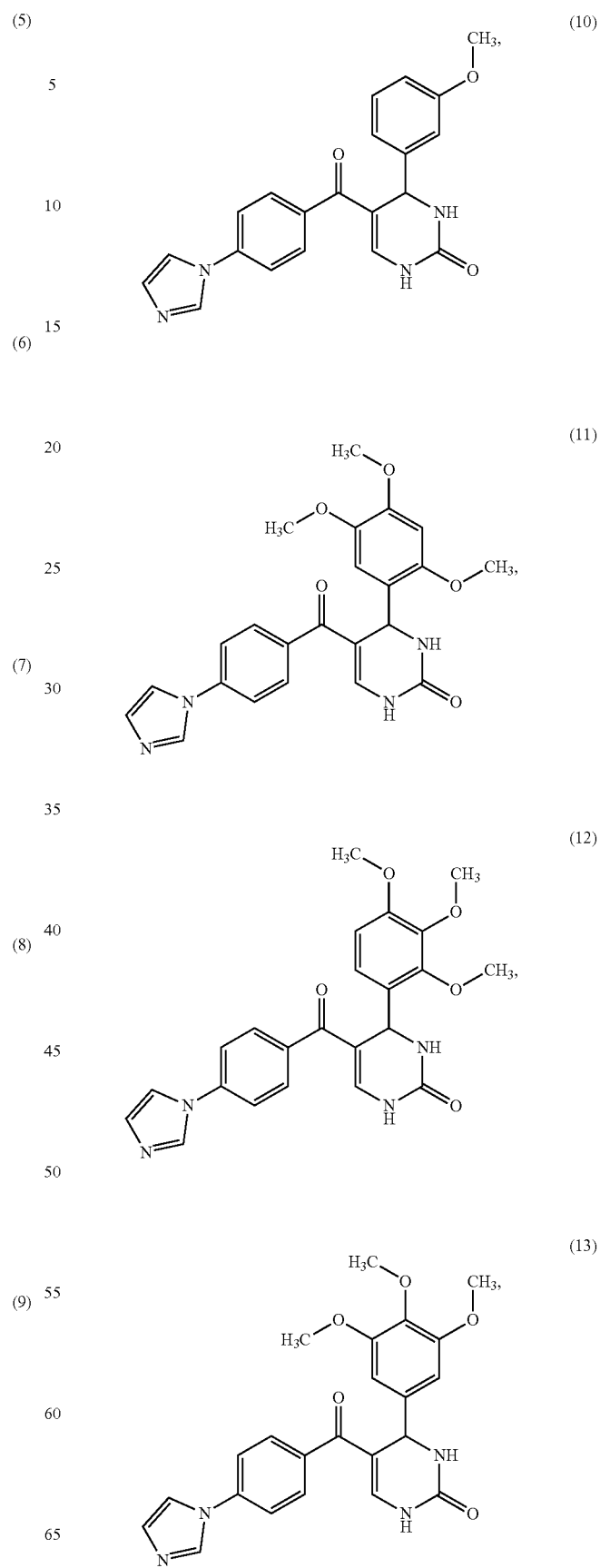

-continued (14)

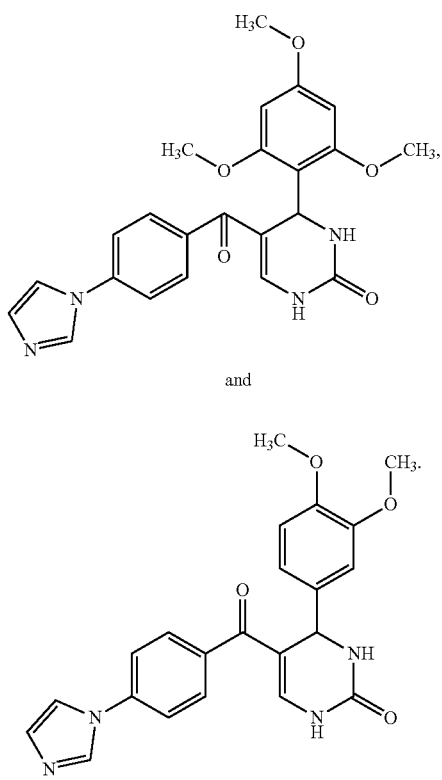

and (15)

5. A method of making a dihydropyrimidinone derivative of Formula 1, comprising:

refluxing 1-[4-(1H-imidazol-1-yl)phenyl]ethan-1-one with dimethylformamide dimethylacetal (DMF-DMA) to obtain enaminone; and refluxing a solution including enaminone, substituted benzaldehyde and urea to yield the dihydropyrimidinone derivative:

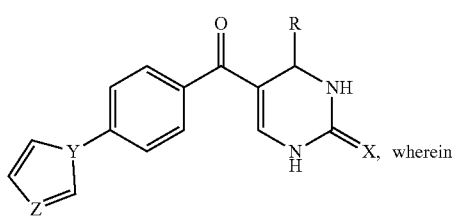

Formula 1

Z is N;
Y is N;
X is selected from O and S; and
R is selected from the group consisting of 2-nitro phenyl, 3-nitrophenyl, 4-nitrophenyl, 4-chlorophenyl, 2,4-dichlorophenyl, 3,4-dimethoxyphenyl, 2-methoxyphenyl, 4-hydroxyphenyl, 3-hydroxyphenyl, dimethylaminophenyl, 3-methoxy phenyl, 4-ethoxyphenyl, 2,4,5-trimethoxyphenyl, 2,3,4-trimethoxyphenyl, 3,4,5-trimethoxyphenyl, 2,4,6-trimethoxyphenyl and 2,4-dimethoxyphenyl, or pharmaceutically acceptable salt thereof.

Z is N;
Y is N;
X is O; and
R represents a substituted phenyl, wherein the substituted phenyl has one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, and arylamino, or and pharmaceutically acceptable salt thereof.

6. The method of claim 5, wherein R is mono-substituted phenyl or di-substituted phenyl.

7. The method of claim 5, wherein R is selected from the group consisting of 2-nitro phenyl, 3-nitrophenyl, 4-nitrophenyl, 4-chlorophenyl, 2,4-dichlorophenyl, 3,4-dimethoxyphenyl, 2-methoxyphenyl, 4-hydroxyphenyl, 3-hydroxyphenyl, dimethylaminophenyl, 3-methoxy phenyl, 4-ethoxyphenyl, 2,4,5-trimethoxyphenyl, 2,3,4-trimethoxyphenyl, 3,4,5-trimethoxyphenyl, 2,4,6-trimethoxyphenyl and 2,4-dimethoxyphenyl.

8. The method of claim 5, wherein the 1-[4-(1H-imidazol-1-yl)phenyl]ethan-1-one is refluxed with dimethylformamide dimethylacetal (DMF-DMA) under a solvent free condition for about 10 hours.

9. The method of claim 5, wherein the solution including enaminone, substituted benzaldehyde, and urea further includes Glacial acetic acid and is refluxed for about 3 hours.

10. The method of claim 5, further comprising:
recrystallizing the dihydropyrimidinone derivative from an ethanol and Glacial acetic acid mixture.

11. A dihydropyrimidinone derivative is a compound of Formula 1:

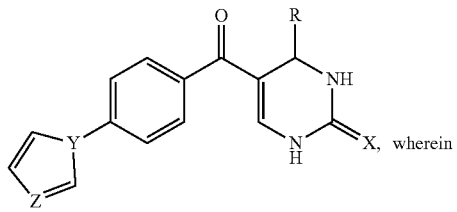

Formula 1

* * * * *